(12) United States Patent
Chattopadhyay et al.

(10) Patent No.: US 6,437,154 B1
(45) Date of Patent: Aug. 20, 2002

(54) PROCESS FOR THE PREPARATION OF 10-DEACETYLBACCATIN III

(75) Inventors: Sunil Kumar Chattopadhyay; Sachin Srivastava; Vijay Kumar Mehta, all of Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/963,768

(22) Filed: Sep. 28, 2001

(51) Int. Cl.$^7$ .............................................. C07D 305/14
(52) U.S. Cl. ...................................... 549/510; 549/511
(58) Field of Search .................................. 549/510, 511

(56) References Cited

U.S. PATENT DOCUMENTS

| 5,412,116 A | 5/1995 | Murray et al. |
| 5,856,532 A | 1/1999 | Chattopadhyay et al. |
| 6,028,206 A | 2/2000 | Chattopadhyay et al. |

FOREIGN PATENT DOCUMENTS

| EP | 0 629 701 A1 | 12/1994 |
| EP | 0 668 360 A1 | 8/1995 |
| GB | 1 241 565 A | 1/2000 |

OTHER PUBLICATIONS

European Search Report, Jan. 30, 2002, Ref. No. NF 413/01–RTM.

*Primary Examiner*—Ba K. Trinh
(74) *Attorney, Agent, or Firm*—Burns, Doane, Swecker & Mathis, L.L.P.

(57) ABSTRACT

The present invention discloses a process for the conversion of a mixture of taxol analogues 7-xylosyl-10-deacetylbaccatin taxols of the formula 2

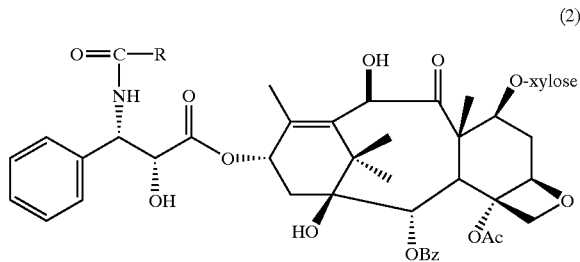

(2)

where R is $C_6H_5$, $CH_3C=CHCH_3$ or $C_5H_{11}$ into 10-deacetylbaccatin III of the formula 1

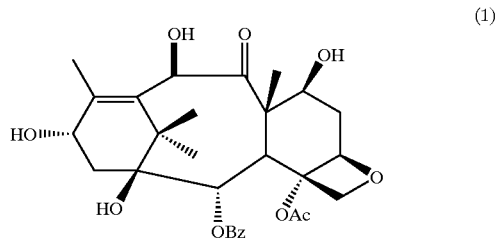

(1)

by dissolving the taxol analogue of formula 2 in a polar solvent, reacting the resultant solution with a base at a temperature of 20–50° C. for a time period in the range of 20–40 hours, and isolating 7-xyloxyl-10-deacetylbaccatin III, dissolving the 7-xylosyl-10-deacetylbaccatin III in a polar solvent, reacting the resultant solution with a periodate at 20–40° C. for a time period in the range of 20–40 hours to cleave the diol system of the xyloside into dialdehyde, treating the generated dialdehyde in an organic acid medium with salts of amine at 0–40° C. for 12–18 hours and isolating 10-deacetylbaccatin III of formula 1.

12 Claims, No Drawings

PROCESS FOR THE PREPARATION OF 10-DEACETYLBACCATIN III

FIELD OF THE INVENTION

The present invention relates to a process for the preparation of 10-deacetylbaccatin III. More particularly, the present invention relates to a process for the preparation of 10-deacetylbaccatin III of the formula 1

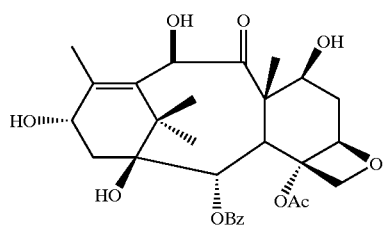
(1)

from taxol analogues of the formula 2 where R is $C_6H_5$, $CH_3C=CHCH_3$ or $C_5H_{11}$.

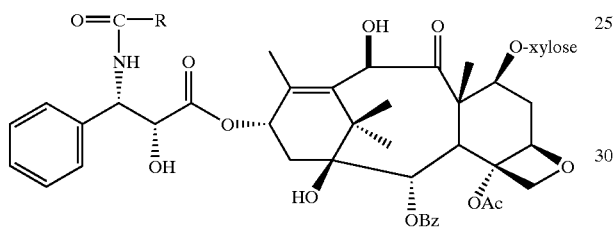
(2)

BACKGROUND OF THE INVENTION

The anticancer drug taxol and its precursor 10-deacetylbaccatin III have been isolated from Himalayan yew *Taxus wallichiana* [S. K. Chattopadhayay et al, Indian J. Chem., 33, B, 409–411 (1994)]. 10-deacetylbaccatin (10-DAB) is a very important precursor as it is used as a starting material for the semi-synthesis of taxol and another important anti-cancer drug taxotere.

It has recently been found that taxol analogues 7-xylosyl-10-deacetyl taxols of the formula 2 are important precursors of taxol and 10-deactyl taxols since they can be converted into the above taxols through chemical conversion procedures [Chattopadhyay et al, U.S. Pat. Nos. 5,856,532 and 6,028,206].

Prior art literature is silent on any process for the conversion of the taxol analogues 7-xylosyl-10-deacetyl taxols of formula 2 into 10-deacetylbaccatin III of formula 1.

OBJECTS OF THE INVENTION

The main object of the invention is to provide a process for the conversion of taxol analogues of the formula 2 into 10-deacetylbaccatin III of formula 1.

It is another object of the invention to provide an economical process for the conversion of taxol analogues of the formula 2 into 10-deacetylbaccatin III of the formula 1.

It is a further object of the process to provide a process for the conversion of taxol analogues of the formula 2 into 10-deacetylbaccatin III of the formula 1 in good yield.

It is another object of the invention to provide a process for the conversion of taxol analogues of the formula 2 into 10-deacetylbaccatin III of the formula 1 which is commercially viable.

SUMMARY OF THE INVENTION

A process has been developed for the conversion of a mixture of taxol analogues 7-xylosyl-10-deacetylbaccatin taxols of the formula 2 where R is $C_6H_5$, $CH_3C=CHCH_3$ or $C_5H_{11}$ into 10-deacetylbaccatin III of the formula 1 by dissolving the taxol analogue of formula 2 in a polar solvent, reaction the resultant solution with a base at a temperature of 20–50° C. for a time period in the range of 20–40 hours, and isolating 7-xylosyl-10-deacetylbaccatin III, dissolving the 7-xylosyl-10-deacetylbaccatin III in a polar solvent, reacting the resultant solution with a periodate at 20–40° C. for a time period in the range of 20–40 hours to cleave the diol system of the xyloside into dialdehyde, treating the generated dialdehyde in an organic acid medium with salts of amine at 0–40° C. for 12–18 hours and isolating 10-deacetylbaccatin III of formula 1.

Accordingly, the present invention provides a process for the preparation of 10-deacetylbaccatin III of the formula 1

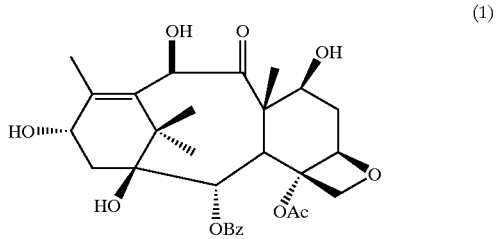
(1)

(a) by dissolving a taxol analogue of the formula 2

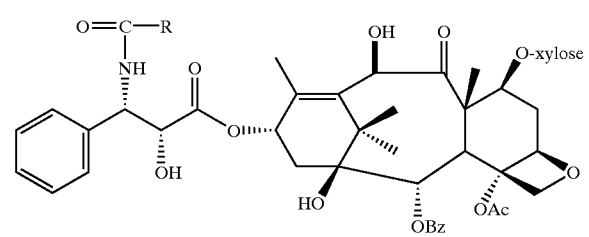
(2)

wherein R is selected from the group consisting of $C_6H_5$, $CH_3C=CHCH_3$ or $C_5H_{11}$ or a mixture thereof in a polar solvent;

(b) treating the resultant solution with a base at a temperature in the range of 20–40° C. for a time period in the range of 2–24 hours to obtain 7-xylosyl-10-deacetylbaccatin III;

(c) isolating 7-xylosyl-10-deacetylbaccatin III;

(d) dissolving the 7-xylosyl-10-deacetylbaccatin III so isolated in step (c) in a polar solvent;

(e) reacting the solution of 7-xylosyl-10-deacetylbaccatin III with a periodate at a temperature in the range of 20–40° C. for a time period in the range of 20–40 hours to obtain a dialdehyde;

(f) treating the dialdehyde so obtained with salts of amine in an organic acid medium at 0–40° C. for a time period in the range of 12–18 hours; and (g) isolating the 10-deacetylbaccatin III of formula 1.

In one embodiment of the invention, the polar solvent used in steps (a) through (d) above is an alkanol selected from the group consisting of methanol, ethanol, propanol and butanol.

In a further embodiment of the invention, the alkanol solvent used is preferably ethanol.

In another embodiment of the invention, the base used in step (b) is selected from hydrazine hydrate and hydroxyl amine.

In a further embodiment of the invention, the base used in step (b) is preferably hydrazine hydrate.

In another embodiment of the invention, the isolation of the products in steps (c) and (f) is done by chromatography using adsorbents selected from silica gel, flurosil, celite and alumina.

In another embodiment of the invention, the periodate used in step (e) is selected from sodium periodate and potassium periodate.

In a further embodiment the invention the periodate used in step (e) is preferably sodium periodate.

In another embodiment the organic acid used in step (f) is selected from the group consisting of acetic acid, propionic acid and methane sulphonic acid.

In a further embodiment of the invention, the organic acid used in step (f) is preferably acetic acid.

In another embodiment of the invention, the amine salt used in step (f) is selected from the group consisting of phenylhydrazine hydrochloride, hydrazine hydrochloride and hydroxyl amine hydrochloride.

In a further embodiment of the invention, the amine salt used in step (f) comprises hydroxyl amine hydrochloride.

DETAILED DESCRIPTION OF THE INVENTION

The present invention provides a novel process for the preparation of 10-deacetylbaccatin III of the formula 1

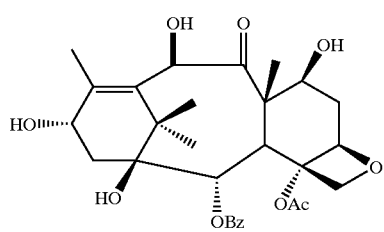

(1)

from taxol analogues of the formula 2 where R is $C_6H_5$, $CH_3C=CHCH_3$ or $C_5H_{11}$. The starting material 7-xylosyl-10-deacetyl taxols used in the above conversion reaction can be isolated from the stem bark of *Taxus wallichiana* by process described in U.S. Pat. No. 5,856,532 (Chattopadhyay et al).

The process of the present invention comprises dissolving the taxol analogue of formula 2 wherein R is selected from the group consisting of $C_6H_5$, $CH_3C=CHCH_3$ or $C_5H_{11}$ or a mixture thereof

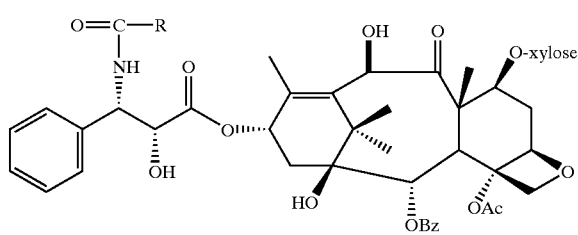

(2)

in a polar solvent, reaction the resultant solution with a base at a temperature of 20–50° C. for a time period in the range of 20–40 hours, and isolating 7-xylosyl-10-deacetylbaccatin III, dissolving the 7-xylosyl-10-deacetylbaccatin III in a polar solvent, reacting the resultant solution with a periodate at 20–40° C. for a time period in the range of 20–40 hours to cleave the diol system of the xyloside into dialdehyde, treating the generated dialdehyde in an organic acid medium with salts of amine at 0–40° C. for 12–18 hours and isolating 10-deacetylbaccatin III of formula 1.

The polar solvent used in steps (a) through (d) is an alkanol such as methanol, ethanol, propanol and butanol, ethanol being the most preferred solvent. The base used in step (b) is generally hydrazine hydrate or hydroxyl amine, preferably hydrazine hydrate.

The product in step (c) 7-xyloxyl-10-deacetylbaccatin is preferably isolated by chromatography using adsorbents selected from silica gel, flurosil, celite and alumina, preferably silica gel.

The periodate used in step (e) is selected from sodium periodate and potassium periodate, preferably sodium periodate. The organic acid used in step (f) is selected from the group consisting of acetic acid, propionic acid and methane sulphonic acid, preferably acetic acid.

In another embodiment of the invention, the amine salt used in step (f) is selected from the group consisting of phenylhydrazine hydrochloride, hydrazine hydrochloride and hydroxyl amine hydrochloride, preferably hydroxyl amine hydrochloride.

Similar to step (a), the polar solvent used in step (d) is also an alkanol such as methanol, ethanol, propanol and butanol, ethanol being the most preferred solvent. The product in step (g) is isolated using chromatography using adsorbents selected from silica gel, flurosil, celite and alumini, preferably silica gel.

A significant feature of this invention is that acid is not used for the periodate oxidation thereby enhancing the yield of the 10-deacetylbaccatin III of formula 1. The starting materials are also cheaply available rendering the process of the invention economical and commercially feasible. Another factor which enhances the commercial viability of the invention is that extreme conditions are not required for the conversion process in order to increase the yield. The mixture of 7-xylosyl-10-deacetyl taxols of formula 2 present in *Taxus wallichiana* provide upto 2.2 g of 10-deacetylbaccatin III per kilogram of the plant material when used in the process of the invention. No process reported in the prior art provides for this level of high yield.

The invention will now be described in greater detail with reference to the following examples which are illustrative and should not be construed as limiting the scope of the invention in any manner. Modifications and variations are possible within the scope of the invention without departing from the spirit of the invention.

EXAMPLE 1

Production of 10-deacetylbaccatin III

To a reaction flask was added a mixture of 7-xylosyl-10-deacetyl taxols of the formula 2 (100 mg) in ethanol (10 ml) and the resulting solution was treated with hydrazine hydrate (1 ml) at 20–50° C. for 2–24 hours with stirring. The reaction mixture was diluted with water and extracted with ethyl acetate (3×50 ml). The ethyl acetate phase was washed with brine, dried over anhydrous sodium sulphate and concentrated in vacuo to residue. The residue was purified by column chromatography over silica gel eluted first with chloroform-methanol (98:2) and then with the same solvent mixture with a ratio of 95:5. The eluent of the latter fraction was concentrated to give a residue of 7-xylosyl-10-deacetylbaccatin III (30 mg). It was then dissolved in methanol (5 ml) and treated with sodium periodate (100 mg in 1 ml of water) and the reaction mixture was stirred for 20–40 hours at 20–40° C. The reaction mixture was diluted with water and extracted with ethyl acetate (3×30 ml). The ethyl acetate phase was washed with water, dried over anhydrous sodium sulphate and concentrated 1 vacuo to a residue. The residue was dissolved in acetic acid and was treated with phenyl hydrazine hydrochloride (50 mg) at 0–40° C. for 12 hours with stirring. The reaction mixture was diluted with water and extract with chloroform (2×50 ml). The chloroform layer was washed with water (2×50 ml), dried over anhydrous sodium sulphate and concentrated in vacuo to give a residue of 10-deacetylbaccatin III (22 mg) and was found to be identical with an authentic sample in all respects (S. K. Chattopadhyay, Indian J. Chem. 33B, 409–411, 1994).

EXAMPLE 2

Production of 10-deacetylbaccatin III

To a reaction flask was added a mixture of 7-xylosyl-10-deacetyl taxols of the formula 2 (100 mg) in methanol (10 ml) and the resulting solution was treated with hydroxyl amine (1 ml) at 20–50° C. for 2–24 hours with stirring. The reaction mixture was worked up as described in example 1 and the residue of 7-xylosyl-10-deacetylbaccatin III was purified by chromatography over florosil to give a pure product (30 mg). It was then dissolved in ethanol (5 ml) and treated with potassium periodate (95 mg in 1 ml water) and the reaction mixture was stirred for 20–40 hours at 20–40° C. It was then worked up as described in example 1 to give a residue which was dissolved in propionic acid and was treated with hydrazine hydrochloride (50 mg) at 0–40° C. for 12–18 hours with stirring. The reaction mixture was worked up as described in example 1 and the residue of 10-deacetylbaccatin III was purified by chromatography over florosil to give a pure product of 10-deacetylbaccatin III (22 mg) which was found to be identical with an authentic sample in all respects (S. K. Chattopadhyay, Indian J. Chem. 33B, 409–411, 1994).

ADVANTAGES OF THE INVENTION

1. The chemicals used for the conversion of 7-xylosyl-10-deacetyl taxols of formula 2 into the 10-deacetylbaccatin III of formula 1 are cheap and readily available. Thus the process is cost effective on commercial scale production.
2. The yield of the product is high—to amounts not reported in the art so far.
3. The non-use of acid in the periodate oxidation step enhances the yield of 10-deacetylbaccatin III.
4. Extreme reaction conditions are not required to effect conversion of 7-xylosyl-10-deacetyl taxols to 10-deacetylbaccatin III thereby rendering the process economical and commercially available.

We claim:
1. A process for the preparation of 10-deacetylbaccatin III of the formula 1 by

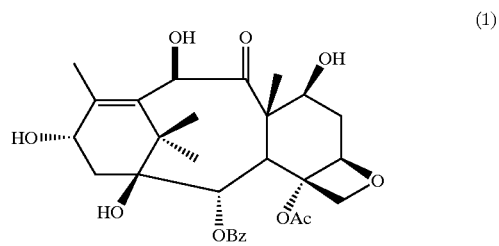

(a) dissolving a taxol analogue of the formula 2

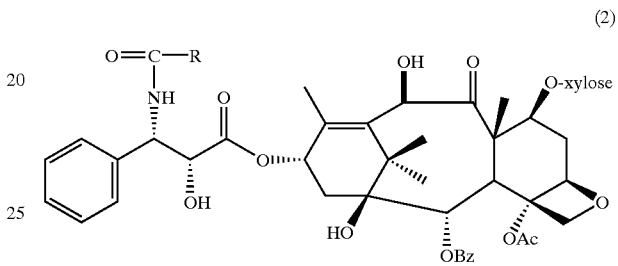

wherein R is selected from the group consisting of $C_6H_5$, $CH_3C=CHCH_3$ or $C_5H_{11}$ or a mixture thereof in a polar solvent;

(b) treating the resultant solution with a base at a temperature in the range of 20–40° C. for a time period in the range of 2–24 hours to obtain 7-xylosyl-10-deacetylbaccatin III;

(c) isolating 7-xylosyl-10-deacetylbaccatin III;

(d) dissolving the 7-xylosyl-10-deacetylbaccatin III so isolated in step (c) in a polar solvent;

(e) reacting the solution of 7-xylosyl-10-deacetylbaccatin III with a periodate at a temperature in the range of 20–40° C. for a time period in the range of 20–40 hours to obtain a dialdehyde;

(f) treating the dialdehyde so obtained with salts of amine in an organic acid medium at 0–40° C. for a time period in the range of 12–18 hours; and (g) isolating the 10-deacetylbaccatin III of formula 1.

2. A process as claimed in claim 1 wherein the polar solvent used in steps (a) and (d) is an alkanol selected from the group consisting of methanol, ethanol, propanol and butanol.

3. A process as claimed in claim 2 wherein the alkanol used is ethanol.

4. A process as claimed in claim 1 wherein the base used in step (b) is selected from hydrazine hydrate and hydroxyl amine.

5. A process as claimed in claim 4 wherein the base used in step (b) is hydrazine hydrate.

6. A process as claimed in claim 1 wherein the isolation of the products in steps (c) and (f) is done by chromatography using adsorbent selected from silica gel, fluorosil, celite and alumina.

7. A process as claimed in claim 1 wherein the periodate used in step (e) is selected from sodium periodate and potassium periodate.

8. A process as claimed in claim 7 wherein the periodate used in step (e) is preferably sodium periodate.

9. A process as claimed in claim 1 wherein the organic acid used in step (f) is selected from the group consisting of acetic acid, propionic acid and methane sulphonic acid.

10. A process as claimed in claim 9 wherein the organic acid used in step (f) is preferably acetic acid.

11. A process as claimed in claim 1 wherein the amine salt used in step (f) is selected from the group consisting of phenylhydrazine hydrochloride, hydrazine hydrochloride and hydroxyl amine hydrochloride.

12. A process as claimed in claim 11 wherein the amine salt used in step (f) comprises hydroxyl amine hydrochloride.

* * * * *